United States Patent [19]
Griffith et al.

[11] 4,045,815
[45] Aug. 30, 1977

[54] SYSTEM FOR COMBINING ANALOG AND IMAGE SIGNALS INTO A STANDARD VIDEO FORMAT

[75] Inventors: James M. Griffith; Walter L. Henry, both of Bethesda, Md.

[73] Assignee: The United States of America as represented by the Secretary of the Department of Health, Education and Welfare, Washington, D.C.

[21] Appl. No.: 655,262

[22] Filed: Feb. 4, 1976

[51] Int. Cl.² .......................................... H04N 5/22
[52] U.S. Cl. ........................... 358/183; 128/2.06 G; 358/93; 340/324 AD
[58] Field of Search ................ 178/6, 6.8, DIG. 6, 178/DIG. 8; 340/324 A, 324 AD; 358/93, 111, 141, 142, 183; 128/2.06 G

[56] References Cited
U.S. PATENT DOCUMENTS

| 3,765,009 | 10/1973 | Graves | 340/324 A |
| 3,798,366 | 3/1974 | Hunt | 178/DIG. 8 |
| 3,898,644 | 8/1975 | Baxter | 178/DIG. 6 |
| 3,909,818 | 9/1975 | Dalke | 340/324 AD |
| 3,954,098 | 5/1976 | Dick | 128/2.05 Z |

Primary Examiner—Howard W. Britton
Attorney, Agent, or Firm—Browdy and Neimark

[57] ABSTRACT

A system for combining at least one analog signal, such as EKG signal, and an image signal, such as video signal representing a fluoroscopic view of a patient's heart or the like. The system includes a summing amplifier, which provides an input to a TV monitor and/or video recorder. The first input to the summing amplifier is provided from a TV camera arranged to view a physiological activity. A second input to the summing amplifier is provided from an encoder which receives one analog signal representing physiological data. The encoder includes an analog-to-digital (A/D) converter which receives the analog signal and feeds it to a random access memory (RAM). The A/D converter and the RAM are controlled by sync signals derived from a master camera control unit, which also provides sync signals to the TV camera.

11 Claims, 5 Drawing Figures

SYSTEM FOR COMBINING ANALOG AND IMAGE SIGNALS INTO A STANDARD VIDEO FORMAT

FIELD OF THE INVENTION

This invention relates to a system for combining at least one analog signal with an image signal into a standard video format, which can be displayed on a conventional TV monitor. The invention relates, more particularly, to a system for combining at least one analog signal, representative of physiological data, with a video signal, representative of a physiological activity, into a standard video format which can be readily displayed on a conventional TV monitor or recorded on a conventional video recorder.

Investigators, therapists and diagnosticians can directly visualize and evaluate relationships between images and dynamic physiological variables.

BACKGROUND OF THE INVENTION

Medical research and practice produce a large amount of information which must be displayed and recorded as a sequence of pictures; these derive typically, for example, from fluoroscopy, nuclear medicine, two-dimensional ultrasonic examination, and activity monitoring. For many such applications closed circuit television has provided an excellent approach to displaying sequences of pictures. However, physiological data, such as EKG, blood pressure, blood flow or respiration representing signals are often concurrently available but have heretofore not been easily displayed on video monitors It is known to display signals representing physiological data on cathode ray oscilloscopes. A prior art system for displaying electrocardiographic (EKG) signals on a cathoderay oscilliscope is described in U.S. Pat. No. 3,853,119 to Peterson et al., issued Dec. 10, 1974. An analog EKG signal is digitalized, stored in a memory for a predetermined period of time and then reconverted back into analog EKG signal for application to the vertical deflection inputs of the oscilliscope. The delay of the signal using the digital electronic circuitry provides requisite flexibility so that it may be utilized to display real time EKG signals or high speed EKG signals which have been collected and are being played back. The system disclosed in the fore-mentioned patent to Peterson et al. does not provide for the simultaneous viewing by a therapist, investigator or diagnostician of a fluoroscopic or ultrasonic image of the heart of the patient from whom the electrocardiographic signals are derived, a distinct disadvantage.

A prior art system employing video equipment for monitoring of body function activities has been described in the U.S. Pat. No. 3,613,669 to Corbin et al., issued Oct. 19, 1971. In this known system a plurality of body function activities such as cardiac conditions are monitored from a remote station. Electrical signal representations of each activity, produced by conventional sensors and/or pairs of leads, are stored temporarily in a storage oscilliscope. A visual display of the electrical signal representations appears on the face of the oscilliscope. A vidicon TV camera scans the visual display of such signals, its output video signals being distributed to a number of remote viewing stations. At each viewing station, the video signals are fed to a conventional TV monitor. No provision is made for viewing simultaneously an image of an ongoing physiological activity, such as a fluoroscopic or ultrasonic image of a patient's beating heart.

It has been proposed to modify systems for remote monitoring of body function activities of the type disclosed in the fore-mentioned patent to Corbin et al. by providing an additional vidicon TV camera and operatively arranging it to scan an image of an ongoing physiological activity, such as an image of a beating heart produced on the screen of a fluoroscope or the like. The outputs from the two vidicon TV cameras are combined in a conventional video mixer and thereafter fed to a common TV monitor. While the physiological data and physiological activity image can be viewed on a single TV monitor, several disadvantages and shortcomings remain. The thus expanded system requires two TV camers, two intermediate visual display means, one of them being a rather complex storage oscilliscope. The thus modified system is complex, expensive and unwieldly.

SUMMARY OF THE INVENTION

It is an object of the invention to provide a system for combining at least one analog signal with an image signal for display on a common TV monitor which avoids any need for providing a plurality of television cameras to develop a composite video signal.

It is another object of the present invention to provide a system for combining at least one analog signal with an image signal for display on a common TV monitor which does not require the conversion of the analog signal into a separate visible display prior to combining the signal with an image signal.

It is an additional object of the present invention to provide a system for combining at least one analog signal with an image signal for display on a common TV monitor which avoids the need for the use of a storage oscilliscope.

It is a further object of the present invention to provide a system for combining at least one analog signal with an image signal for display on a common TV monitor which does not require a conversion of the analog data into digital form and subsequently back to analog form.

It is yet another object of the present invention to provide a system for combining at least one analog signal, representative of physiological data, with an image signal, representative of a physiological activity for display on a common TV monitor which is particularly suitable for use by medical investigators, therapists, and diagnosticians and avoids in large measure the disadvantages and shortcomings of the more complex prior art systems.

The foregoing objects, as well as others which are to be made clear from the text below, are achieved in accordance with the present invention by providing a system for combining at least one analog signal with an image signal which includes a summing amplifier having a first input constituted by a video signal for a TV camera, which can be operatively positioned to scan a fluoroscopic image or the like. A second input to the summing amplifier is provided from an encoder which encodes an analog signal, such as may be produced by EKG sensors, into a video signal. The encoder and the TV camera are controlled from the same master camera control unit. Those composite video signal from the summing amplifier may be coupled to a conventional TV monitor. If desired, the output from the summing amplifier can be fed directly to a video recorder having a playback means.

DESCRIPTION OF THE PREFERRED EMBODIMENTS

Figure 1:
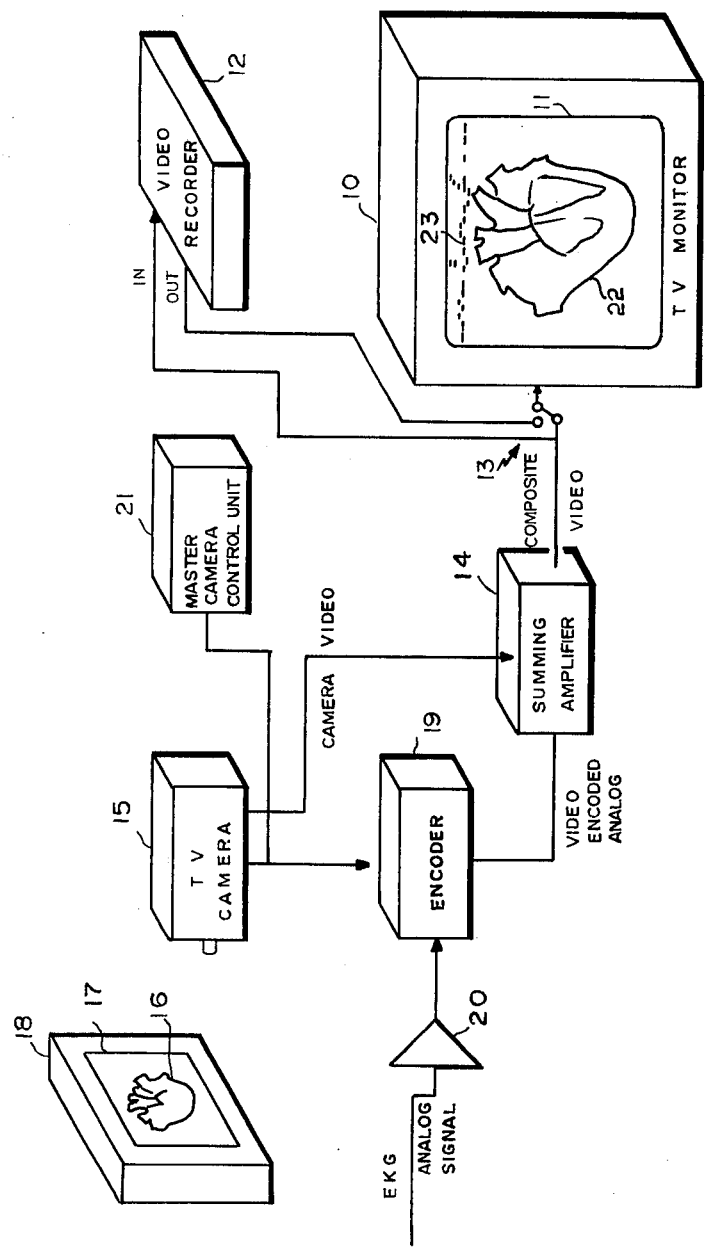
FIG. 1 is a diagrammatic, block diagram of a system for combining an analog signal representing physiological data with an image representing a physiological acitivity according to an exemplary embodiment of the present invention in combination with a TV monitor and a video recorder.

As illustrated in FIG. 1, a system for combining at least one analog signal, such as an EKG signal, with an image signal, such as a fluoroscopic view of a patient's heart, includes a conventional TV monitor 10 having a viewing face 11. A conventional, video recorder 12 having playback capability has its output coupled to the video input terminal of the monitor 10 via one input terminal of a single-pole, double-throw switch 13. The other terminal of the switch 13 is connected to the output terminal of a linear, video summing amplifier 14 which is also connected to the video input terminal of the video recorder 12. Thus, it is possible to display on the face 11 of the TV monitor 10, depending on the position of the switch 13, either a composite video signal from the summing amplifier 14 or video signals being played back from the video recorder 12.

As illustrated, the video summing amplifier 14 is provided with two video input signals. The first video input signal is a camera video signal provided from a conventional TV camera 15 which is arranged to scan a physiological activity or a visual image of such activity, such as a fluoroscopic image 16 of a patient's heart appearing on a screen 17 of a fluoroscope 18. The second video input signal is a video encoded analog signal from an encoder 19 which received at least one analog signal representing physiological data, in the illustrative embodiment an EKG signal, via a variable gain amplifier 20. It is to be appreciated that more than one analog signal may be fed to the encoder 19, for example, a plurality of analog signals from various pairs of EKG electrodes could be fed to the encoder 19 for encoding into a video format.

A master camera control unit 21 is provided for supplying vertical and horizontal sync signals to the TV camera 15 and to the encoder 19 to ensure that the two video inputs to the summing amplifier 14 are synchronized. In operation, the composite video signal from the summing amplifier 14 is converted in the TV monitor 10 into a visible display on its face 11, an image 22 of the patient's beating heart being visible on a portion of the face 11 and an image 23 corresponding to the EKG analog signal being visible on a different portion.

The resolution provided by the system is a function of the video system bandwidth and the number of lines per field or frame. In a practical embodiment good resolutions can be achieved using a general purpose vidicon camera as the TV camera 15 with a standard commercial scanning line rate of 525 lines per second per frame, consisting of two interlaced fields of 262.5 lines, the field rate being 60 fields per second. The maximum amplitude resolution is determined by the number of television lines employed which actually appear on the face 11 of the monitor 10, approximately 485 lines being utilized for visual display in standard commercial television.

Although virtually any amount of data can be recorded on video tape, the number of cycles of physiological data which can be readily observed on the TV monitor 10 using the standard commercial scanning rates mentioned above is limited. As a practical matter, the limit is about 320 samples per frame, assuming one sample is to be placed in each column because typical video systems using the line and frame rates mentioned above are designed to resolve about 320 vertical lines. In practice the sampling system must employ a sampling frequency at least twice as high as the highest significant frequency present in the data. Although the bandwidth of commercial video systems is typically much higher than that of the analog data signals being superimposed on camera video images, the bandwidth remains a limiting factor because several seconds of analog signal must be compressed into approximately 53 $\mu$ seconds, the visible width of the television picture.

Figure 2:
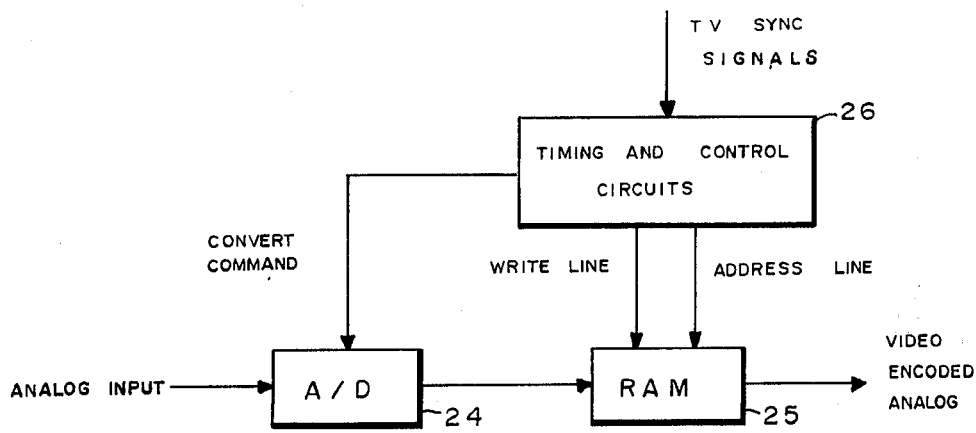
FIG. 2 is a block diagram of an encoder which may be used as the encoder in the system illustrated in FIG. 1.

The encoder 19 (FIG. 1), as shown in more detail in FIG. 2, includes an analog-to-digital (A/D) converter 24 which receives the analog signal representing physiological data from the variable gain amplifier 20 (FIG. 1). The received analog signal is converted in the converter 24 into a digital signal which is fed to a random access memory (RAM) 25. The converter 24 and the random access memory 25 are controlled by timing and control circuits 26. The timing and control circuits 26, which are shown in detail in FIG. 3, receive vertical and horizontal sync signals from the master camera control unit 21 (FIG. 1) and produce a convert command signal and a plurality of row and line address signals which are fed respectively to the converter 24 and to the random access memory 25. The random access memory 25 also receives a write signal from the timing and control circuits 26.

It is to be appreciated that the random access memory 25 is easily partitioned as a matrix with each element of the matrix corresponding to a respective position on the face 11 of the TV monitor 10. The matrix is constructed using the television raster lines to define the rows and an oscillator to define the columns. When a new sample is taken, it is placed in the right-hand column and old samples are effectively shifted one column to the left. While not essential, the digital data is shifted through the random access memory 25 by changing the order in which the columns are read. This avoids the problem of actually moving the memory content. If it is desired to use the whole vertical face 11 (FIG. 1) for display of the physiological data, each television visible scanning line is digitally encoded and assigned a respective amplitude value. Sample points are placed in an appropriate row (television line) after analog to digital conversion. In the event it is desired to use only a portion of the height of the face 11 of the TV monitor 10 for the display of the physiological data, only a portion of the scanning lines are assigned amplitude values. Similarly, if only a portion of the width of the face 11 of the television monitor 10 is to be devoted to the display of the physiological data sample points are assigned only to rows which correspond, for example, to the left or right halves of the face 11 of the monitor 10.

Figure 3:
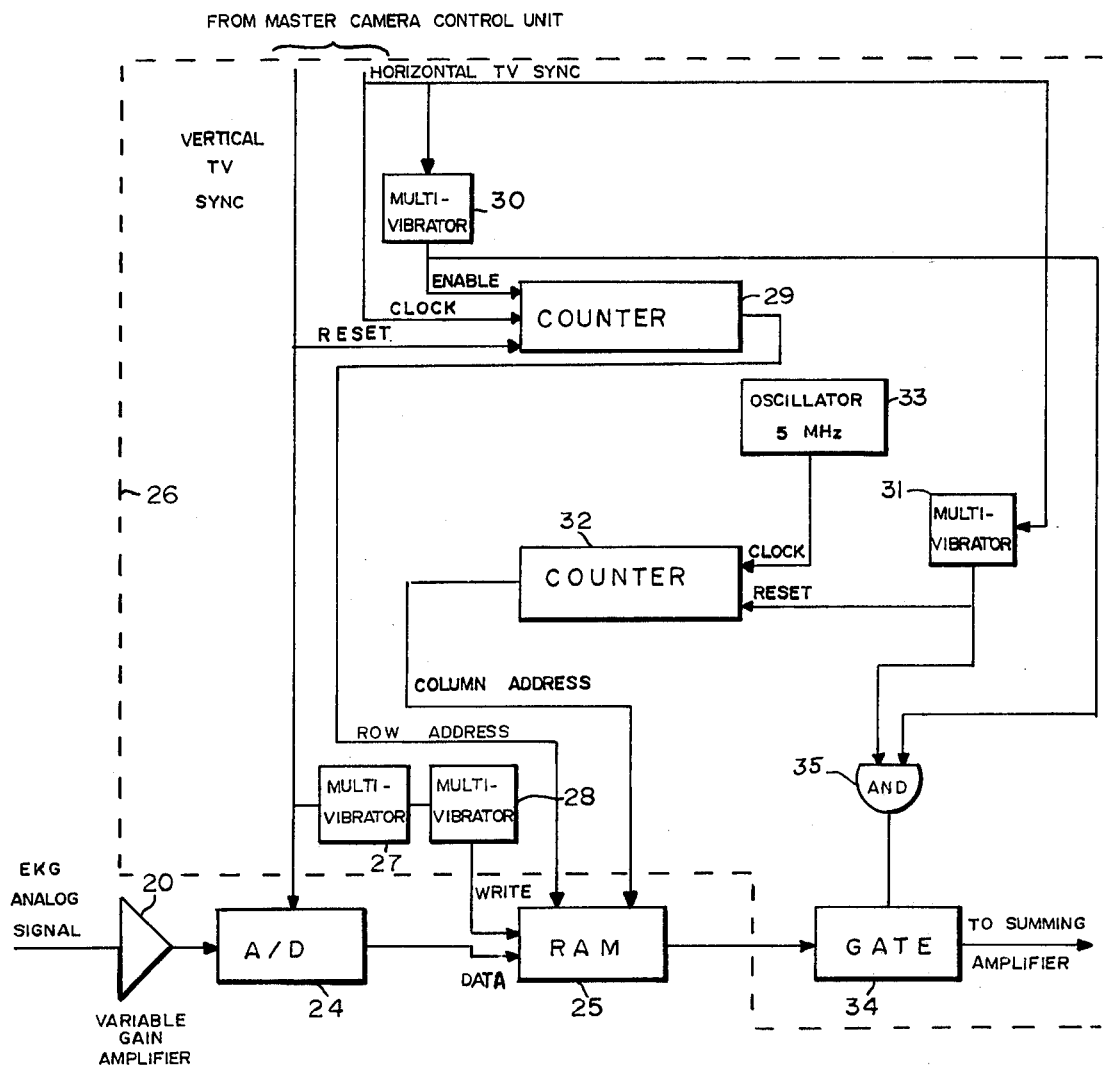
FIG. 3 is a detailed block diagram of timing and control circuits which can be used in the circuit illustrated in FIG. 2.

In FIG. 3, details of the timing and control circuits 26 are shown with the amplifier 20, the converter 24 and the random access memory 25. The timing and control circuits 26 include a sync signal lead which provides a strobe signal or convert command to the converter 24, this signal being the vertical TV sync signal provided from the master camera control unit 21 (FIG. 1). The vertical TV sync signal is also fed to a one-shot multivibrator 27, which provides a delay sufficient to allow output from the converter 24 to appear. The multivibrator 27 has its output coupled to a further one-shot multivibrator 28 which supplies its output signal as a WRITE command to the random access memory 25. The WRITE command signal enables the random access memory 25 to store the digital signals which arrive from the converter 24 during each television field, as determined by the vertical sync signals.

The vertical sync signal is also fed as a RESET signal to the reset input terminal of a counter 29. The counter 29 is provided with a CLOCk input signal and an ENABLE input signal. The CLOCK input signal is the horizontal TV sync signal supplied directly from the master camera control unit 21 (FIG. 1), the ENABLE signal being supplied from a one-shot multivibrator 30 which is connected to receive at its input the horizontal TV sync signal from the master camera control unit 21 (FIG. 1). The period of the multivibrator 30 is such that its output enables the counter 29 for periods corresponding to the time period of each horizontal scanning line appears on the face 11 of the monitor 10 (FIG. 1).

The output signals from the counter 29 are coupled, via address leads, as row address signals to the random access memory 25, these address signals determining the particular row in the randon access memory 25 respective particular inputs from the converter 24 are to be stored.

Figure 5:
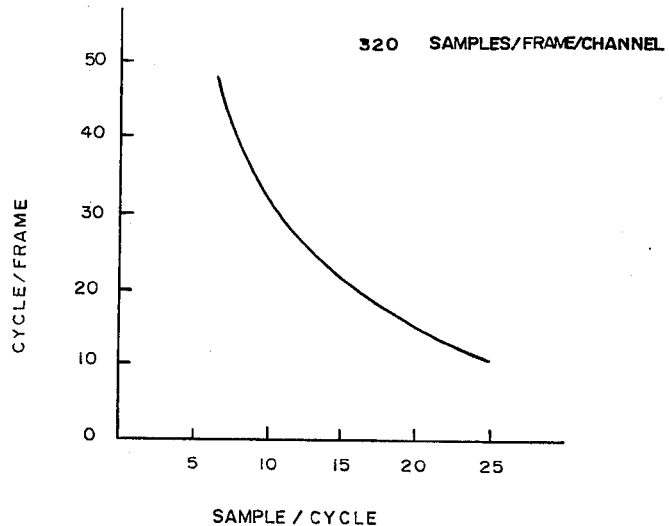
FIG. 5 is a graphical representation showing the relationship between samples per cycle and cycles per frame for a resolution of 320 samples per frame per channel in a system according to the present invention.

The horizontal TV sync signal is also directly applied to the input of a one-shot multivibrator 31 which has its output connected to the RESET input of a counter 32. The counter 32 is provided with a CLOCK input from an adjustable variable frequency oscillator 32 which is illustrated as a 5 MH$_z$ oscillator. The frequency of the oscillator 33 is adjustable so that some flexibility in the horizontal display can be provided to accommodate different cyclic rates. For example as shown in FIG. 5, if the same resolution of 320 samples per frame per channel is desired, and the cycles per frame were doubled, the oscillator frequency would be halved. In another aspect, were it desired to display the physiologic data on, for example, only the left or right halves of the face 11 (FIG. 1) with a resolution of 320 samples per frame, the oscillator frequency of the oscillator 33 would be doubled.

The output signals from the counter 29 are coupled, via address leads, as column address signals to the random access memory 25, these signals determining the particular row in the random access memory 25 respective particular inputs from the converter 24 are to be stored.

The video encoded analog signals from the random access memory 25 are fed to a controlled signal gate 34, which has its output fed to the summing amplifier 14 (FIG. 1). The gate 34 is opened by a control signal received from an AND circuit 35 having two inputs. The two inputs to the AND circuit 35 are provided respectively from the outputs of the multivibrator 30 and 31. Thus, at the times the counter 29 and the counter 32 are being enabled and reset respectively, the gate 35 is enabled and provides for the digital signals stored in the random access memory to be fed to the summary amplifier 14 (FIG. 1) and thence to the monitor 10 and to the recorder 12.

Figure 4:
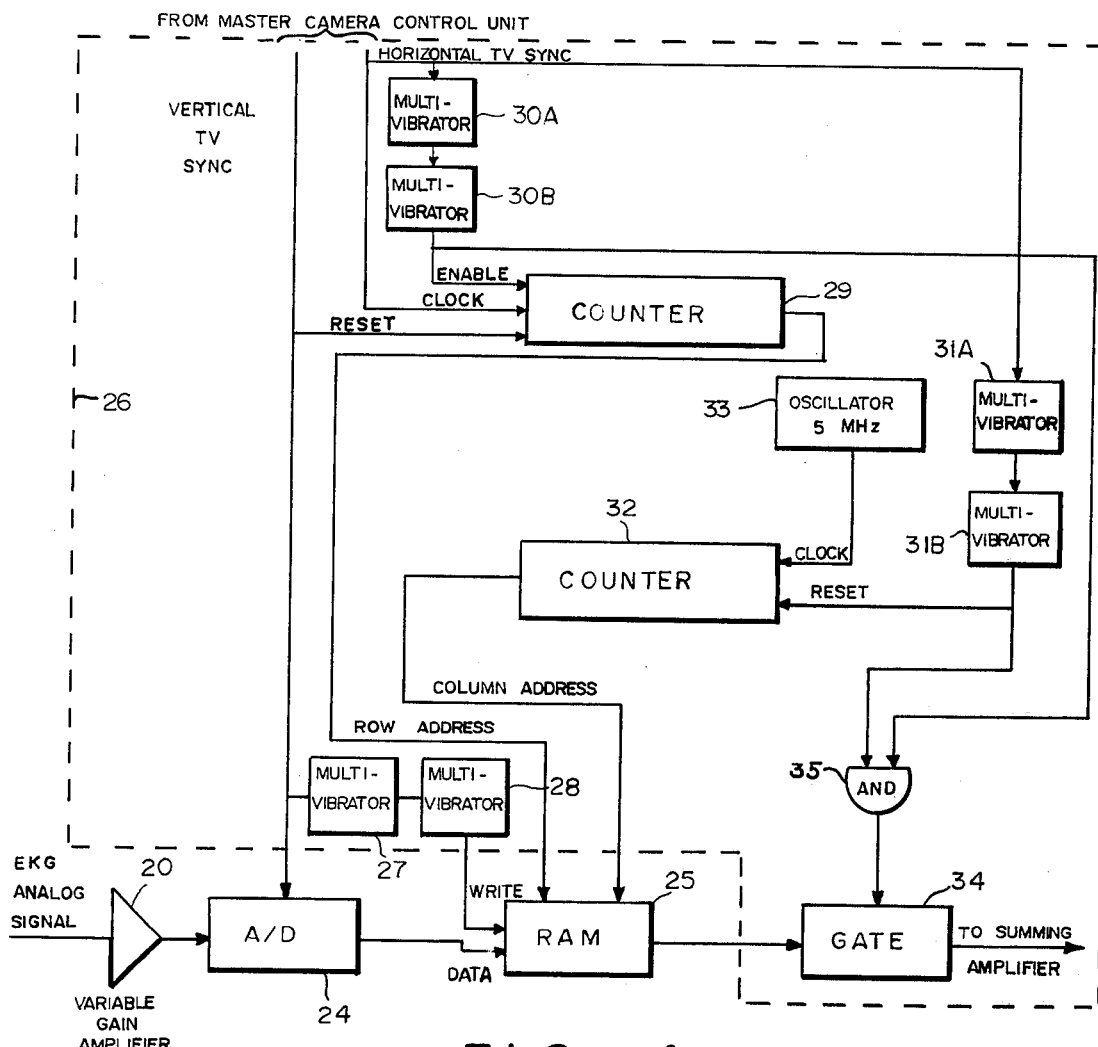
FIG. 4 is a detailed block diagram of the preferred timing and control circuits which can be used in the circuit illustrated in FIG. 2 to provide greater adaptability over the relative placement of the image and analog signal on the face of the TV monitor.

The timing and control circuits shown in FIG. 4 are similar to those of FIG. 3, corresponding reference numerals designating corresponding identical parts. The circuits of FIG. 4 operate in much the same manner as the circuits of FIG. 3 and consequently need not be dicussed in detail. It is to be noted that the only two differences in structure between the circuits if FIG. 4 and FIG. 3 involve respectively a substitution of two cascaded one-shot multivibrators 30A and 30B for the multivibrator 30 and a substitution of two cascaded one-shot multivibrators 31A and 31B for the multivibrator 31. The periods of the one-shot multivibrators 30A, 30B, 31A and 31B are preferably made adjustable. As a result of such adjustability, the converted physiological data can be placed on various portions of the face 11 of the TV monitor 10 by simply adjusting the periods of the four multivibrators. The on time of the multivibrator 30A determines the left limit of possible display of data on the face 11, and the off time of the multivibrator 30B determines the right limit of possible display of data on the face 11. The upper limit and the lower limit of display of data on the face 11 are determined respectively by the on time of the multivibrator 31A and the off time of the multivibrator 31B.

The operation of the system according to the present invention can be easily carried out by persions who are not skilled in electronics. Once the number of sampling points per line or frame has been decided upon and the particular TV system, so far as scanning ratio are concerned, has been selected. An investigator therapist or diagnostician would simply turn the system on, place a patient whose beating heart is to be studied in such a position that a fluoroscopic image of his heart could be viewed on the screen 17 of the fluoroscope 18 and arrange a sensor or pair of leads to provide an analog EKG signal as an input to the amplifier 20. The TV camera 15 would be placed to scan the fluoroscopic image 16 of the patient's heart on the fluoroscopic screen 17. The gain of the amplifier 20 would be adjusted to provide for a conveniently sized viewable display of the trace 23, which corresponds to the EKG analog signal, on the face 11 of the TV monitor 10. As a practical matter, the gain of the variable amplifier 20 would be adjusted so that the trace 23 would not cover the full vertical extent of the face 11, but would be of sufficient magnitude to be meaningful to the person using the system.

If it was desired to separate the image 22 of the patient's heart as it appears on the monitor 10 from the trace 23, it is only necessary to move the TV camera 15 accordingly to provide separation, albeit in some cases an overlay of the trace 23 on the image 22 would not be objectionable. Of course, the periods of the multivibrators 30A, 30B, 31A and 31B (FIG. 4) could also be made to position the trace 23 with respect to the image 22 of the heart.

The encoder 19, under control of the horizontal and vertical sync signals converts the EKG analog signal from the amplifier 20 into a video signal which is combined with the camera video signal from the camera 15 into a composite video signal in the summing amplifier 14. As illustrated the composite video output from the summing amplifier 14 is fed to the video recorder 12 and to the monitor 10 on which appears the visual image 22 of the patient's heart and the trace 23 representing the EKG analog signal; as a practical matter about 2 seconds or cycles of the cardiac information of the EKG signal are displayed on the face 11 of the monitor 10, the trace 23 to the viewer seeming to move constantly to the left so that the most recent signal information appears on the right, while the oldest viewable signal information moves to the left and off of the face 11.

It is to be understood that while the foregoing description and accompanying drawing figures are concerned mainly with a single channel system that it is possible to adapt the present invention so as to multiplex two or more signal outputs from converters for storage in the random access memory; in which case the memory could be compartmentalized into sections so that separate traces, corresponding to different but concurrently available analog signals, would appear at different vertical levels on the TV monitor face. Although the present invention has been described and illustrated mainly using an EKG analog input signal, it is to be appreciated that the analog signal or signals need not be of a cardiac nature or even from an organism. In fact, nonorganism sources of an analog signal or signals and non-physiological sources of activity images are contemplated to be within the scope of the present invention.

Although the present invention has been described and illustrated with reference to particular embodiments of systems for combining and converting signals, it is to be appreciated that other embodiments and varients are possible within the spirit and scope of the present invention, its scope being defined in the appended claims.

What is claimed is:

1. A system for combining at least one analog signal with video signals comprising:
   an analog-to-digital converter having an analog signal input means and an enabling signal input means;
   a random access memory having a data input means coupled to said analog-to-digital for receiving its digital output, said random access memory having a write input means, a row address input means and a column address input means;
   a controlled gate circuit means having its data signal input means coupled to said random access memory for receiving its output, said gate circuit means having a control signal input means;
   a source of vertical and horizontal sync signals;
   first multivibrator means, second multivibrator means and third multivibrator means;
   means coupling vertical sync signals from said source to said enabling signal input means of said analog-to-digital converter for enabling same upon occurrence of each vertical sync signal;
   means coupling vertical sync signals from said source to an input of said first multivibrator means, said write input means of said random access memory being coupled to said first multivibrator means;
   a first counter means having an enable input means, a clock input means and a reset input means, means for coupling vertical sync signals from said source to said reset input of said first counter means, means for coupling horizontal sync signals from said source to said clock input means of said first counter means, and means for coupling said enable input means of said first counter means to an output of said second multivibrator means, said second multivibrator means having its input means coupled to said source for receiving horizontal sync signals therefrom, and said row address input means of said random access memory being coupled to said first counter means for receiving its output signals;
   oscillator means;
   a second counter means having a clock input means coupled to said oscillator means for receiving output signals therefrom and having reset input means coupled to said third multivibrator means for receiving output signals therefrom, said third multivibrator means having its input means coupled to said source for receiving vertical sync signals therefrom, and said column address input means of said random access memory being coupled to said second counter means for receiving its output signals;
   logic circuit means having a first input coupled to said third multivibrator means for receiving its output signals and having a second input coupled to said second multivibrator means for receiving its output signals, said logic circuit having its output coupled to said control signal input means of said gate circuit means for enabling said gate circuit;
   an additional source supplying video signals; and
   means coupled to said additional source and to said gate circuit means for combining signals therefrom.

2. A system according to claim 1, further comprising monitor means coupled to said summing means and responsive to its output for displaying the composite video.

3. A system according to claim 1, wherein said additional source of video signals comprises a TV camera.

4. A system according to claim 1, including a source of said one analog signal, said source of analog signal being means responsive to a physiological activity.

5. A system according to claim 1, wherein said source of said one analog signal is a source of an analog EKG signal.

6. A system according to claim 1, wherein said logic circuit means consists of an AND circuit.

7. A system according to claim 1, wherein said first multivibrator means consists of two one-shot multivibrators coupled in series between said write input means of said random access memory and said source of sync signals.

8. A system according to claim 1, wherein said third multivibrator consists of two one-shot multivibrators coupled in series between said first input of said logic circuit means and said source of sync signals.

9. A system according to claim 1, wherein said first, second and third multivibrator means consist respectively of respective pairs of series connected one-shot multivibrators.

10. A system according to claim 1, wherein said second multivibrator means consists of two one-shot multivibrators coupled in series between said enable input means of said first counter means and said source of sync signals.

11. A system according to claim 10, wherein said third multivibrator means consists of two additional one-shot multivibrators coupled in series between said first input of said logic circuit means and said source of sync signals.

* * * * *